(12) United States Patent
Yuan

(10) Patent No.: US 12,286,393 B2
(45) Date of Patent: *Apr. 29, 2025

(54) METHOD FOR REFINING BIO-BASED PROPYLENE GLYCOL

(71) Applicant: Changchun Meihe Science and Technology Development Co., Ltd., Changchun (CN)

(72) Inventor: Yi Yuan, Changchun (CN)

(73) Assignee: Changchun Meihe Science and Technology Development Co., Ltd., Changchun (CN)

(*) Notice: Subject to any disclaimer, the term of this patent is extended or adjusted under 35 U.S.C. 154(b) by 0 days.

This patent is subject to a terminal disclaimer.

(21) Appl. No.: 18/155,597

(22) Filed: Jan. 17, 2023

(65) Prior Publication Data
US 2023/0150904 A1    May 18, 2023

Related U.S. Application Data

(63) Continuation of application No. 17/280,595, filed as application No. PCT/CN2019/106551 on Sep. 19, 2019, now Pat. No. 11,578,024.

(30) Foreign Application Priority Data

Sep. 29, 2018  (CN) .......................... 201811151458.1

(51) Int. Cl.
| | |
|---|---|
| C07C 29/82 | (2006.01) |
| B01D 3/36 | (2006.01) |
| C07C 29/86 | (2006.01) |

(52) U.S. Cl.
CPC ................ C07C 29/82 (2013.01); B01D 3/36 (2013.01); C07C 29/86 (2013.01)

(58) Field of Classification Search
CPC ............ B01D 3/36; C07C 29/82; C07C 29/86
See application file for complete search history.

(56) References Cited

U.S. PATENT DOCUMENTS

| | | |
|---|---|---|
| 4,935,102 A | 6/1990 | Berg |
| 5,423,955 A | 6/1995 | Berg |

(Continued)

FOREIGN PATENT DOCUMENTS

| | | |
|---|---|---|
| CN | 107001206 | 8/2017 |
| CN | 108191608 | 6/2019 |

OTHER PUBLICATIONS

International Search Report for PCT/CN2019/106551, issued Dec. 20, 2019.

*Primary Examiner* — Jonathan Miller
(74) *Attorney, Agent, or Firm* — King & Spalding

(57) ABSTRACT

The invention provides a process for refining bio-based propylene glycol, wherein impurities having boiling points close to that of propylene glycol are separated. In this process, $C_5$-$C_{20}$ oleophilic alcohol compounds, $C_5$-$C_{20}$ alkanes and/or $C_4$-$C_{20}$ oleophilic ketone compounds are subjected to azeotropism as an azeotropic solvent together with the bio-based propylene glycol to obtain an azeotrope containing propylene glycol. Then the azeotropic solvent in the azeotrope is separated to obtain a crude propylene glycol which is further purified to obtain propylene glycol.

14 Claims, 2 Drawing Sheets

(56) References Cited

U.S. PATENT DOCUMENTS

| | | |
|---|---|---|
| 5,425,853 A | 6/1995 | Berg |
| 8,197,645 B2 | 6/2012 | Diefenbacher |
| 9,926,251 B2 | 3/2018 | Zhang |
| 10,081,584 B2 | 9/2018 | Fischer |
| 10,308,577 B2 | 6/2019 | Perez Golf |
| 11,578,024 B2 * | 2/2023 | Yuan .................. C07C 29/86 |
| 2017/0327446 A1 | 11/2017 | Zhang |
| 2017/0362150 A1 | 12/2017 | Fischer |
| 2018/0079871 A1 * | 3/2018 | Tudman .................. C08G 18/48 |
| 2019/0060782 A1 | 2/2019 | Shimizu |
| 2019/0062244 A1 | 2/2019 | Perez Golf |
| 2019/0202764 A1 | 7/2019 | Fischer |

* cited by examiner

METHOD FOR REFINING BIO-BASED PROPYLENE GLYCOL

CROSS REFERENCE TO RELATED APPLICATIONS

This application is a continuation of U.S. patent application Ser. No. 17/280,595, which is a national phase application under 35 U.S.C. § 371 of International Application No. PCT/CN2019/106551, filed Sep. 19, 2019, which claims priority to Chinese Patent Application No. 201811151458.1, filed Sep. 29, 2018. The contents of each of the above-identified applications is hereby fully incorporated herein by reference.

TECHNICAL FIELD

The invention relates to a process for refining propylene glycol, in particular relates to a process for refining bio-based propylene glycol comprising impurities having boiling points close to that of propylene glycol, such as butanediol, pentanediol.

BACKGROUND ART

In recent years, technologies for production of propylene glycol from raw materials of biomass have developed rapidly because of the uncertainty of oil prices and people's attention to sustainable development. However, by-products different from those in the petroleum routes to produce propylene glycol, for example, impurities having boiling points very close to that of propylene glycol, such as butanediol, pentanediol, hexanediol, propylene carbonate, are produced during the production of propylene glycol in biomass routes due to differences in synthetic routes. A traditional method for purification of liquid-phase compounds is a rectification process for separation by using different boiling points of substances. However, the boiling points of these impurities are close to that of propylene glycol, for example, impurities including butanediol, pentanediol, hexanediol, propylene carbonate which have similar physical properties to propylene glycol and boiling points very close to that of propylene glycol. Therefore, separation of propylene glycol from these impurities having very close boiling points by a direct rectification method would lead to a low distillation yield of propylene glycol and high energy consumption.

U.S. Pat. Nos. 4,935,102, 5,423,955 both describe technologies of separating propylene glycol from butanediol by using different azeotropic solvents. An azeotropic solvent has an azeotropic point with propylene glycol. Generally, the temperature of an azeotropic point is apparently lower than the boiling point of propylene glycol. Thus, a distinct temperature difference is produced between the boiling point of an azeotrope of propylene glycol and an azeotropic solvent and the boiling point of impurities such as butanediol. The separation of propylene glycol and butanediol can be achieved economically by means of rectification.

The process of producing propylene glycol in biomass routes will produce impurities other than butanediol, such as pentanediol, hexanediol, propylene carbonate and the like, the boiling points of these impurities being very close to that of propylene glycol. However, the above-mentioned literatures only describe the effects of separation of propylene glycol from butanediol by using an azeotropic solvent, without mentioning the effects of separation of propylene glycol from other impurities having boiling points close to that of propylene glycol such as pentanediol, hexanediol, propylene carbonate and the like after the use of the azeotropic solvent.

Contents of the Invention

The invention provides a process for refining bio-based propylene glycol, wherein impurities having boiling points close to that of propylene glycol are separated. The process can increase the purity of said propylene glycol to 99.50% or more under the condition of a high recovery rate of propylene glycol of 80% or more, preferably 85% or more.

Said bio-based propylene glycol refers to propylene glycol produced from the raw material of biomass. It comprises, but not limited to, propylene glycol, butanediol, pentanediol, hexanediol and optional propylene carbonate. Here said propylene glycol is preferably 1,2-propylene glycol; said butanediol is preferably 1,2-butanediol, said pentanediol is preferably 1,2-pentanediol, and said hexanediol is preferably 1,2-hexanediol.

In the process of the invention, one, two or more of $C_5$-$C_{20}$ oleophilic alcohol compounds, $C_5$-$C_{20}$ alkanes and $C_4$-$C_{20}$ oleophilic ketone compounds are subjected to azeotropism as an azeotropic solvent together with the bio-based propylene glycol to obtain an azeotrope containing propylene glycol, then water is added to dissolve the propylene glycol in the azeotrope, the water-insoluble azeotropic solvent is separated from the propylene glycol aqueous solution, and propylene glycol is obtained from dehydration and refining of the resulting propylene glycol aqueous solution.

In one embodiment of the invention, the $C_5$-$C_{20}$ oleophilic alcohol compounds are preferably $C_6$-$C_{15}$ oleophilic alcohol compounds, more preferably $C_7$-$C_{12}$ oleophilic alcohol compounds, and particularly preferably $C_7$-$C_{10}$ oleophilic alcohol compounds. The oleophilic alcohol compounds may be aliphatic alcohols and alcohols containing heterocycles. For example, examples of the oleophilic alcohol compounds are pentanol and its isomers, hexanol and its isomers, heptanol and its isomers, octanol and its isomers, nonanol and its isomers, decanol and its isomers, undecanol and its isomers, lauryl alcohol and its isomers, and benzyl alcohol. Especially preferably, said oleophilic alcohol compounds are heptanol, n-heptanol, 2-heptanol, octanol, n-octanol, isooctanol, sec-octanol, nonanol, n-nonanol, isononanol, decanol, n-decanol and isodecanol.

In another embodiment of the invention, the $C_5$-$C_{20}$ alkanes are preferably $C_5$-$C_{15}$ alkanes, preferably $C_5$-$C_{12}$ alkanes and particularly preferably $C_5$-$C_9$ alkanes. The alkanes may be straight-chain alkanes, branched alkanes, cycloalkanes or alkanes containing a benzene ring. For example, examples of the alkanes are pentane and its isomers, hexane and its isomers, heptane and its isomers, octane and its isomers, nonane and its isomers, decane and its isomers, undecane and its isomers, dodecane and its isomers, cyclopentane and cyclohexane, ethylbenzene and its isomers. Especially preferably, the alkanes are hexane, heptane, octane, nonane, decane, undecane, dodecane, cyclopentane, cyclohexane and ethylbenzene.

In another embodiment of the invention, the $C_4$-$C_{20}$ oleophilic ketone compounds are preferably $C_5$-$C_{15}$ oleophilic ketone compounds, more preferably $C_6$-$C_{12}$ oleophilic ketone compounds, particularly preferably $C_6$-$C_{10}$ oleophilic ketone compounds. The ketones may be aliphatic ketones or alicyclic ketones. Especially preferably, the ketones are cyclohexanone, heptanone, 4-heptanone, diisobutyl ketone, isophorone, nonanone and 2-nonanone.

The biomass according to the invention preferably refers to edible first generation biomass including corn, sugarcane, etc., and non-food second generation biomass of agricultural and forestry wastes including straw, timber, bagasse, etc. Preferably, the bio-based propylene glycol of the invention comprises, but not limited to, propylene glycol (preferably 1,2-propylene glycol), butanediol (preferably 1,2-butanediol), pentanediol (preferably 1,2-pentanediol), hexanediol (preferably 1,2-hexanediol) and propylene carbonate. The bio-based propylene glycol of the invention optionally comprises propylene glycol. More preferably, said bio-based propylene glycol comprises, but not limited to:

1-100 wt. % of propylene glycol (excluding end point of 100 wt. %), preferably 1-99 wt. % of propylene glycol, more preferably 5-99 wt. % of propylene glycol and particularly preferably 10-95 wt. % of propylene glycol, wherein the propylene glycol is preferably 1,2-propylene glycol;

0-95 wt. %, preferably 0-70 wt. %, more preferably 0-50 wt. %, and particularly preferably 0-30 wt. % of butanediol (preferably 1,2-butanediol, excluding end point of 0);

0-95 wt. %, preferably 0-50 wt. %, more preferably 0-10 wt. %, and particularly preferably 0-1 wt. % pentanediol (preferably 1,2-pentanediol, excluding end point of 0);

0-95 wt. %, preferably 0-50 wt. %, more preferably 0-10 wt. %, and particularly preferably 0-1 wt. % of hexanediol (preferably 1,2-hexanediol, excluding end point of 0), and;

0-95 wt. %, preferably 0-50 wt. %, more preferably 0-10 wt. %, and particularly preferably 0-1 wt. % of propylene carbonate.

Said bio-based propylene glycol further optionally comprises:

0-95 wt. %, preferably 0-50 wt. % of ethylene glycol, and/or;

0-50 wt. %, preferably 0-10 wt. % of 2,3-butanediol.

In the process of the invention, the azeotropic solvent forms an azeotrope by azeotropism with propylene glycol. There is a distinct temperature difference between the boiling point of the azeotrope and that of impurities such as butanediol, pentanediol, hexanediol and propylene carbonate and other impurities having boiling points close to that of propylene glycol. Therefore, propylene glycol can be economically purified, for example, by a rectification process.

The azeotropic solvent can be separated from an aqueous solution containing propylene glycol by an extraction process after mixing the azeotrope with water. Said aqueous solution containing propylene glycol is refined after dehydration to obtain propylene glycol.

MODE OF CARRYING OUT THE INVENTION

Figure 1:
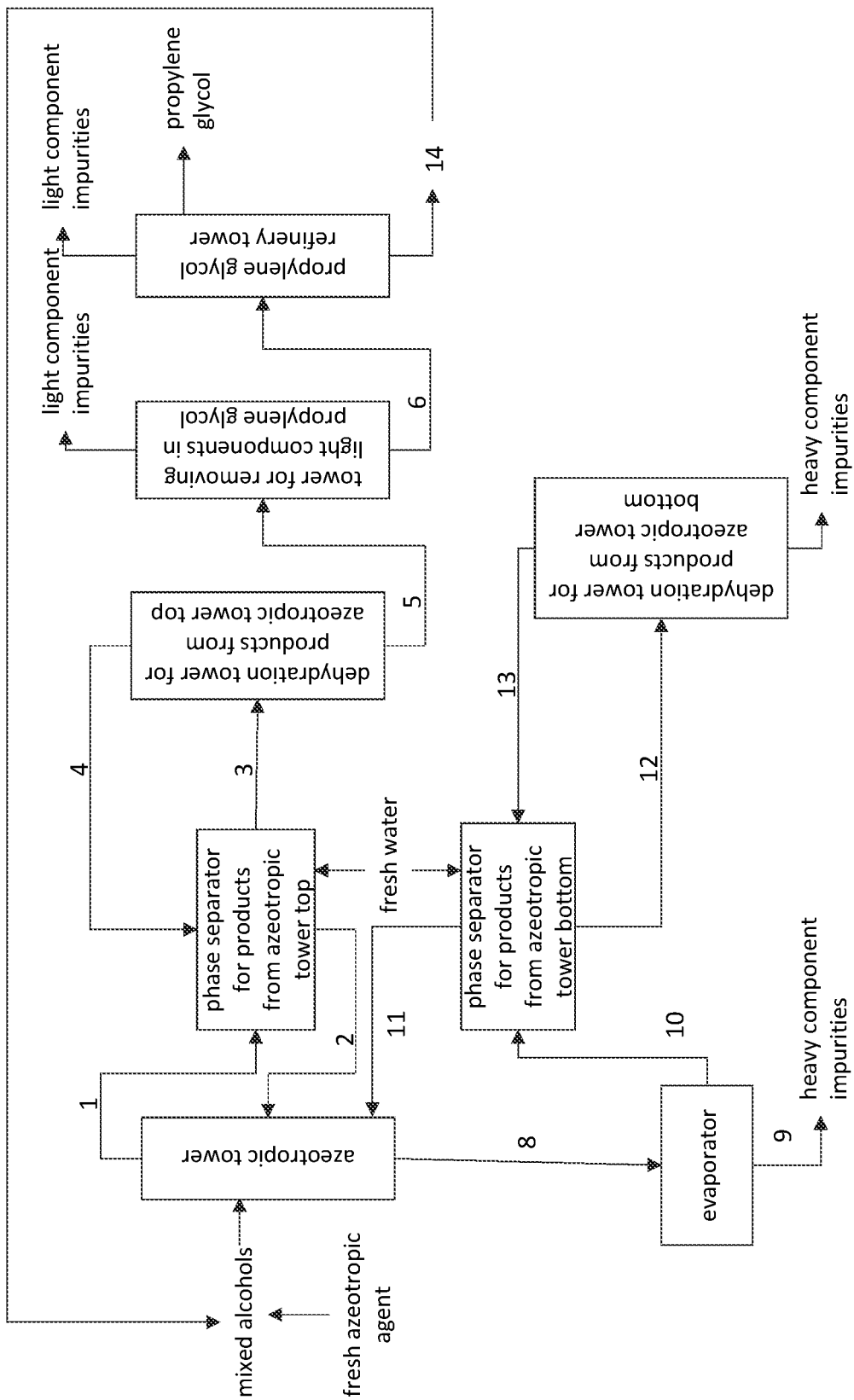
FIG. 1 is a flowchart of azeotropically refining process of the bio-based propylene glycol of the invention.

In combination with FIG. 1, the refining process of the invention is described as follows:
A mixed polyol feed and an azeotropic solvent feed are mixed before entering the azeotropic column, where the azeotropic column is a rectification tower. The weight ratio of the azeotropic solvent feed to propylene glycol of the mixed polyol feed is 0.1:1~20:1, preferably 0.2:1~20:1 and more preferably 0.5:1~20:1. The operating pressure of the azeotropic column is 1 kPa (absolute)-101 kPa (absolute), and the weight ratio of the reflux material to the extracted material in the azeotropic column (i.e., reflux ratio) is 0.1:1~15:1. Therein, most of the propylene glycol and a small amount of other impurities in the mixed polyol feed are extracted from the top of the azeotropic column together with the azeotropic solvent (i.e., stream 1) and enter a Distillate decanter. The heavy impurities including, but not limited to, butanediol, pentanediol, hexanediol and optional propylene carbonate, and a small amount of azeotropic solvent are extracted from the azeotropic column bottom (i.e., stream 8) and enter the evaporator.

Steam 1 and fresh water and optional recycled water (i.e., stream 4) are mixed and stratified in the Distillate decanter. An azeotropic solvent layer (i.e., stream 2) is recycled to the azeotropic column, while the water layer (i.e., stream 3) enters a Water removal column for azeotropic column distillate.

In the Water removal column for azeotropic column distillate, the water in stream 3 is extracted from the top of the tower (i.e., stream 4) and recycled to the Distillate decanter. The crude propylene glycol extracted from the bottom of the tower (i.e., stream 5) enters a MPG light removal column.

After separation of most of the light impurities in the crude propylene glycol (i.e., stream 5) in the MPG light removal column, the crude propylene glycol is extracted from the bottom of the MPG light removal column (i.e., stream 6) and enters the MPG refinery column. Most of the light impurities are extracted from the top of the MPG light removal column.

After removal of the light components, heavy components and residual light components in the crude propylene glycol (i.e., stream 6) are separated in the MPG refinery column. The propylene glycol is extracted from the side line; the residual light components are extracted from the top of the MPG refinery column; the heavy components (i.e., stream 14) are recycled, and mixed with the mixed polyol feed, and then enter the azeotropic column.

The materials in the bottom of the azeotropic column (i.e., stream 8) enter the evaporator, wherein the heavy impurities having extremely high boiling points are separated from the bottom of the evaporator and discharged from the system (i.e., stream 9).

Stream 10 comprising, but not limited to, an azeotropic solvent, butanediol, pentanediol, hexanediol and optional propylene carbonate enters a Bottom decanter. Then it is mixed with fresh water and optional recycled water (i.e., stream 13) and then stratified. Therein, the azeotropic solvent layer (i.e., stream 11) is recycled to the azeotropic column while the water layer (i.e., stream 12) comprising, but not limited to, water, butanediol, pentanediol, hexanediol and optional propylene carbonate enters a Water removal column for azeotropic column bottom for dehydration.

The water in the water layer (i.e., stream 12) of the Bottom decanter is separated in the Water removal column for azeotropic column bottom, extracted from the top of the tower (i.e., stream 13) and then recycled to the Bottom decanter. Impurities comprising, but not limited to, butanediol, pentanediol and hexanediol and optional propylene carbonate are extracted from the bottom of the Water removal column for azeotropic column bottom and discharged from the system.

The technology of the invention can separate the propylene glycol in the bio-based propylene glycol from the impurities comprising, but not limited to, butanediol, pentanediol, hexanediol and optional propylene carbonate under the condition of a high recovery rate of propylene glycol of 80% or more, preferably 85% or more. In the meanwhile, the purity of propylene glycol is improved to 99.50% or more. Hence, the problem that the separation from butanediol, pentanediol, hexanediol and optional propylene carbonate cannot be simultaneously achieved in the existing technology of purification of bio-based propylene glycol is solved.

EXAMPLES

The present invention is further described by the following examples. However, the present invention is not limited thereto.

Example 1

According to the flowchart illustrated in FIG. 1, the mixed polyol feed was the material obtained from the dehydration and the removal of the light components of the mixed product produced from the raw material of biomass. The material was composed of, in percentage by weight, 55.65% of 1,2-propylene glycol, 24.32% of ethylene glycol, 15.24% of 1,2-butanediol, 3.07% of 2,3-butanediol, 0.2% of 1,2-pentanediol, 0.2% of 1,2-hexanediol, 0.1% of propylene carbonate and 1.22% of other light and heavy components.

The mixed polyol feed and the fresh azeotropic solvent isooctanol were mixed and entered the $45^{th}$ theoretical plate of the azeotropic column. The weight ratio of the azeotropic solvent (including fresh azeotropic solvent and recycled azeotropic solvent stream 2 and stream 11) to propylene glycol in the mixed polyol feed was 3.6:1. There were altogether 90 theoretical plates in the azeotropic column. The recycled azeotropic solvent stream 2 from the tower top and the recycled azeotropic solvent stream 11 from the tower bottom entered the azeotropic column from the $40^{th}$ theoretical plate of the azeotropic column respectively. The operating pressure of the azeotropic column was 50 kPa (absolute), and the reflux ratio was 2:1. Stream 1 from the tower top separated by the azeotropic column was composed of an azeotropic solvent, 1,2-propylene glycol, ethylene glycol, 1,2-butanediol, 2,3-butanediol, 1,2-pentanediol, 1,2-hexanediol, propylene carbonate and other light components, respectively in percentage by weight of 69.56%, 19.75%, 8.63%, 0.02%, 0.93%, 0%, 0%, 0%, 1.11%.

Stream 9 of heavy components having a high boiling point was separated from stream 8 by an evaporator.

Stream 10 and stream 13 from the top of the Water removal column for azeotropic column bottom entered the Bottom decanter. The stratified azeotropic solvent layer (i.e., stream 11) which was a recycled azeotropic solvent was recycled to the azeotropic column; the water layer (i.e., stream 12) which was a mixture of alcohol and water entered the Water removal column for azeotropic column bottom for dehydration and the water (i.e., stream 13) was recycled to the Bottom decanter.

Stream 1 from the top of the azeotropic column together with stream 4 from the top of the Water removal column for azeotropic column distillate entered the Distillate decanter. After separation by the phase separator, the water layer stream (i.e., stream 3) entered the Water removal column for azeotropic column distillate for dehydration. After dehydration, stream 5 from the bottom of the tower entered the $60^{th}$ theoretical plate of the MPG light removal column. The MPG light removal column had a total of 90 theoretical plates with a reflux ratio of 80:1 and operating pressure of 10 kPa (absolute). The crude propylene glycol (stream 6) was extracted from the $50^{th}$ theoretical plate of the MPG light removal column and entered the MPG refinery column. The MPG refinery column had a total of 90 theoretical plates with a reflux ratio of 10:1 and an operating pressure of 10 kPa (absolute). The propylene glycol product was extracted from the $10^{th}$ theoretical plate of the MPG refinery column. By analyzing via the method of the national standard GB29216-2012 and ASTM E202 of the USA respectively, the purity of the refined propylene glycol in percentage by weight was 99.61%, and the total rectification yield of propylene glycol was 89.2%.

Example 2

According to the flowchart illustrated in FIG. 1, the mixed polyol feed was the material obtained from the dehydration and the removal of the light components of the mixed product produced from the raw material of biomass in Example 1.

The mixed polyol feed and the fresh azeotropic solvent n-nonanol were mixed and entered the $45^{th}$ theoretical plate of the azeotropic column. The weight ratio of the azeotropic solvent (including fresh azeotropic solvent and recycled azeotropic solvent stream 2 and stream 11) to propylene glycol in the mixed polyol feed was 0.8:1. There were altogether 90 theoretical plates in the azeotropic column. The recycled azeotropic solvent stream 2 from the tower top and the recycled azeotropic solvent stream 11 from the tower bottom entered the azeotropic column from the $40^{th}$ theoretical plate of the azeotropic column respectively. The operating pressure of the azeotropic column was 5 kPa (absolute), and the reflux ratio was 2:1. Stream 1 from the tower top separated by the azeotropic column was composed of an azeotropic solvent, 1,2-propylene glycol, ethylene glycol, 1,2-butanediol, 2,3-butanediol, 1,2-pentanediol, 1,2-hexanediol, propylene carbonate and other light components, respectively in percentage by weight of 33.20%, 49.66%, 13.76%, 0.54%, 1.52%, 0%, 0%, 0%, 1.32%.

Stream 9 of heavy components having a high boiling point was separated from stream 8 by an evaporator.

Stream 10 and stream 13 from the top of the Water removal column for azeotropic column bottom entered the Bottom decanter. The stratified azeotropic solvent layer (i.e., stream 11) which was a recycled azeotropic solvent was recycled to the azeotropic column; the water layer (i.e., stream 12) which was a mixture of alcohol and water entered the Water removal column for azeotropic column bottom for dehydration and the water (i.e., stream 13) was recycled to the Bottom decanter.

Stream 1 from the top of the azeotropic column together with stream 4 from the top of the Water removal column for azeotropic column distillate entered the Distillate decanter. After separation by the phase separator, the water layer stream (i.e., stream 3) entered the Water removal column for azeotropic column distillate for dehydration. After dehydration, stream 5 from the bottom of the tower entered the $60^{th}$ theoretical plate of the MPG light removal column. The MPG light removal column had a total of 90 theoretical plates with a reflux ratio of 80:1 and operating pressure of 10 kPa (absolute). The crude propylene glycol (stream 6) was extracted from the $50^{th}$ theoretical plate of the MPG light removal column and entered the MPG refinery column. The MPG refinery column had a total of 90 theoretical plates with a reflux ratio of 10:1 and an operating pressure of 10 kPa (absolute). The propylene glycol product was extracted from the $10^{th}$ theoretical plate of the MPG refinery column. By analyzing via the method of the national standard GB29216-2012 and ASTM E202 of the USA respectively, the purity of the refined propylene glycol in percentage by weight was 99.64%, and the total rectification yield of propylene glycol was 85.5%.

Example 3

According to the flowchart illustrated in FIG. 1, the mixed polyol feed was the material obtained from the dehydration and the removal of the light components of the mixed product produced from the raw material of biomass in Example 1.

The mixed polyol feed and the fresh azeotropic solvent 2-nonanone were mixed and entered the $45^{th}$ theoretical plate of the azeotropic column. The weight ratio of the azeotropic solvent (including fresh azeotropic solvent and recycled azeotropic solvent stream 2 and stream 11) to propylene glycol in the mixed polyol feed was 3.5:1. There were altogether 90 theoretical plates in the azeotropic column. The recycled azeotropic solvent stream 2 from the tower top and the recycled azeotropic solvent stream 11 from the tower bottom entered the azeotropic column from the $40^{th}$ theoretical plate of the azeotropic column respectively. The operating pressure of the azeotropic column was 70 kPa (absolute), and the reflux ratio was 2.5:1. Stream 1 from the tower top separated by the azeotropic column was composed of an azeotropic solvent, 1,2-propylene glycol, ethylene glycol, 1,2-butanediol, 2,3-butanediol, 1,2-pentanediol, 1,2-hexanediol, propylene carbonate and other light components, respectively in percentage by weight of 70.62%, 20.74%, 8.10%, 0.04%, 0.26%, 0%, 0%, 0%, 0.24%.

Stream 9 of heavy components having a high boiling point was separated from stream 8 by an evaporator.

Stream 10 and stream 13 from the top of the Water removal column for azeotropic column bottom entered the Bottom decanter. The stratified azeotropic solvent layer (i.e., stream 11) which was a recycled azeotropic solvent was recycled to the azeotropic column; the water layer (i.e., stream 12) which was a mixture of alcohol and water entered the Water removal column for azeotropic column bottom for dehydration and the water (i.e., stream 13) was recycled to the Bottom decanter.

Stream 1 from the top of the azeotropic column together with stream 4 from the top of the Water removal column for azeotropic column distillate entered the Distillate decanter. After separation by the phase separator, the water layer stream (i.e., stream 3) entered the Water removal column for azeotropic column distillate for dehydration. After dehydration, stream 5 from the bottom of the tower entered the $60^{th}$ theoretical plate of the MPG light removal column. The MPG light removal column had a total of 90 theoretical plates with a reflux ratio of 80:1 and operating pressure of 10 kPa (absolute). The crude propylene glycol (stream 6) was extracted from the $50^{th}$ theoretical plate of the MPG light removal column and entered the MPG refinery column. The MPG refinery column had a total of 90 theoretical plates with a reflux ratio of 10:1 and an operating pressure of 10 kPa (absolute). The propylene glycol product was extracted from the $10^{th}$ theoretical plate of the MPG refinery column. By analyzing via the method of the national standard GB29216-2012 and ASTM E202 of the USA respectively, the purity of the refined propylene glycol in percentage by weight was 99.55%, and the total rectification yield of propylene glycol was 88.3%.

Example 4

According to the flowchart illustrated in FIG. 1, the mixed polyol feed was the material obtained from the dehydration and the removal of the light components of the mixed product produced from the raw material of biomass in Example 1.

The mixed polyol feed and the fresh azeotropic solvent 4-heptanone were mixed and entered the $45^{th}$ theoretical plate of the azeotropic column. The weight ratio of the azeotropic solvent (including fresh azeotropic solvent and recycled azeotropic solvent stream 2 and stream 11) to propylene glycol in the mixed polyol feed was 12.5:1. There were altogether 90 theoretical plates in the azeotropic column. The recycled azeotropic solvent stream 2 from the tower top and the recycled azeotropic solvent stream 11 from the tower bottom entered the azeotropic column from the $40^{th}$ theoretical plate of the azeotropic column respectively. The operating pressure of the azeotropic column was 70 kPa (absolute), and the reflux ratio was 2.5:1. Stream 1 from the tower top separated by the azeotropic column was composed of an azeotropic solvent, 1,2-propylene glycol, ethylene glycol, 1,2-butanediol, 2,3-butanediol, 1,2-pentanediol, 1,2-hexanediol, propylene carbonate and other light components, respectively in percentage by weight of 89.98%, 7.30%, 2.17%, 0.14%, 0.35%, 0%, 0%, 0%, 0.06%.

Stream 9 of heavy components having a high boiling point was separated from stream 8 by an evaporator.

Stream 10 and stream 13 from the top of the Water removal column for azeotropic column bottom entered the Bottom decanter. The stratified azeotropic solvent layer (i.e., stream 11) which was a recycled azeotropic solvent was recycled to the azeotropic column; the water layer (i.e., stream 12) which was a mixture of alcohol and water entered the Water removal column for azeotropic column bottom for dehydration and the water (i.e., stream 13) was recycled to the Bottom decanter.

Stream 1 from the top of the azeotropic column together with stream 4 from the top of the Water removal column for azeotropic column distillate entered the Distillate decanter. After separation by the phase separator, the water layer stream (i.e., stream 3) entered the Water removal column for azeotropic column distillate for dehydration. After dehydration, stream 5 from the bottom of the tower entered the $60^{th}$ theoretical plate of the MPG light removal column. The MPG light removal column had a total of 90 theoretical plates with a reflux ratio of 80:1 and operating pressure of 10 kPa (absolute). The crude propylene glycol (stream 6) was extracted from the $50^{th}$ theoretical plate of the MPG light removal column and entered the MPG refinery column. The MPG refinery column had a total of 90 theoretical plates with a reflux ratio of 20:1 and an operating pressure of 10 kPa (absolute). The propylene glycol product was extracted from the $10^{th}$ theoretical plate of the MPG refinery column. By analyzing via the method of the national standard GB29216-2012 and ASTM E202 of the USA respectively, the purity of the refined propylene glycol in percentage by weight was 99.58%, and the total rectification yield of propylene glycol was 85.1%.

Comparative Example 1

Figure 2:
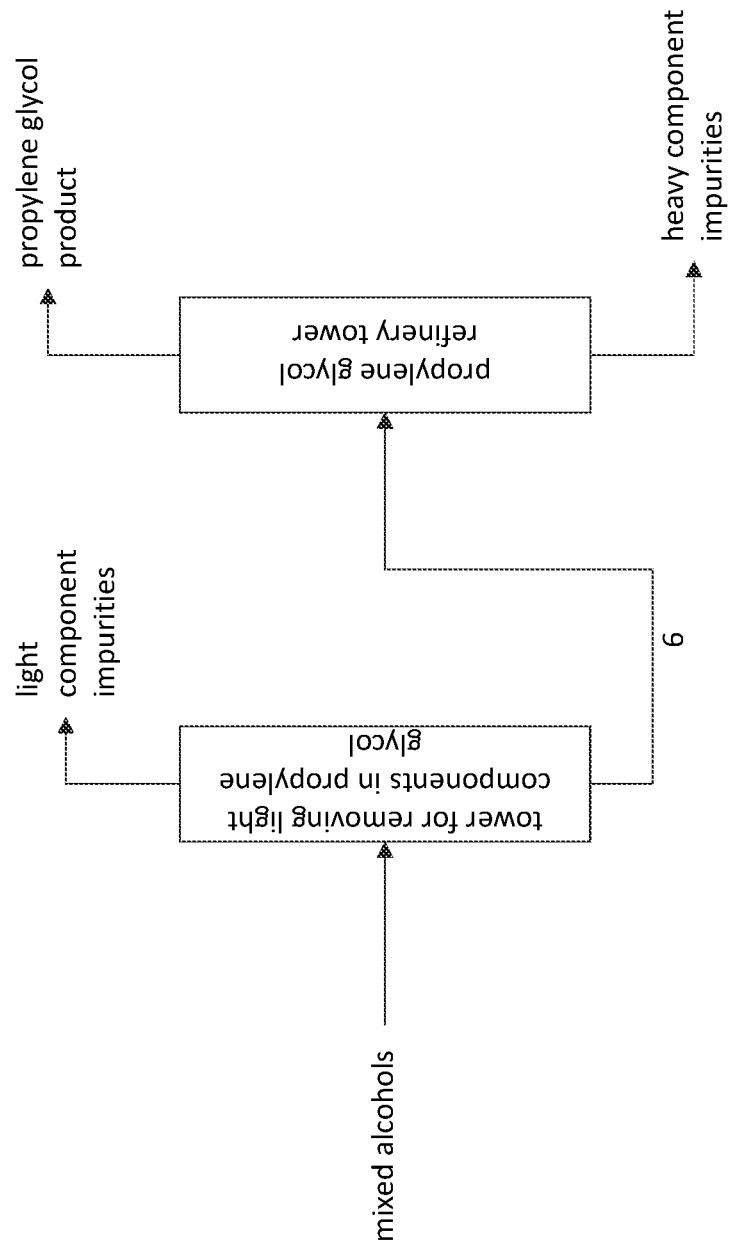
FIG. 2 is a flowchart of traditional rectification process of bio-based propylene glycol.

The material obtained from the dehydration and the removal of light-components of the mixed product produced from the raw material of biomass in Example 1 was used as the mixed polyol raw material. Separation was carried out in the traditional rectification method as illustrated in FIG. 2. Since no azeotropic solvent was added in the traditional rectification process and no azeotropism or extraction section was required, there was no need for an azeotropic column, a Distillate decanter, a Bottom decanter, a Water removal column for azeotropic column distillate, a Water removal column for azeotropic column bottom and an evaporator. Compared with Example 1, the total theoretical plates and the operating conditions in the MPG light removal column and the MPG refinery column in the two processes were the same. The propylene glycol product was composed of 1,2-propylene glycol, ethylene glycol, 1,2-butanediol, 2,3-butanediol, 1,2-pentanediol, 1,2-hexanediol, propylene carbonate and other light and heavy components, in percentage by weight of 97.86%, 0.192%, 0.23%, 0%, 0.01%, 0.01%, 0.01%, 1.688%, respectively. The total rectification yield of lowly pure propylene glycol was 29.0%.

The experimental results show that the traditional rectification without the use of an azeotropic solvent cannot effectively separate the 1,2-butanediol, 1,2-pentanediol, 1,2-hexanediol, propylene carbonate and other light and heavy components in propylene glycol. Increase of the height of the tower, reflux ratio and energy consumption is needed to reach the purity of 99.5%. The process of the invention can effectively increase the purity of said propylene glycol to 99.50% or more under the condition of a high yield of propylene glycol.

The invention claimed is:

1. A process for refining bio-based propylene glycol, comprising:
    (i) mixing one-or more azeotropic solvents with bio-based propylene glycol to obtain an azeotrope-containing propylene glycol feed;
    (ii) subjecting the azeotrope-containing propylene glycol feed to reflux in an azeotropic or rectification tower at a pressure of 1 to 101 kPa (absolute);
    (iii) obtaining extracted material from the top of the azeotropic or rectification tower;
    (iv) adding water to the extracted material to dissolve the propylene glycol in the azeotrope;
    (v) separating the water-insoluble azeotropic solvent- from the propylene glycol aqueous solution;
    (vi) obtaining propylene glycol-from dehydration and refining of the resulting propylene glycol aqueous solution;
wherein the one or more azeotropic solvents comprise nonane and its isomers, undecane and its isomers, and dodecane and its isomers; and
wherein the bio-based propylene glycol comprises propylene carbonate.

2. The process according to claim 1, wherein the bio-based propylene glycol refers to propylene glycol produced from biomass.

3. The process according to claim 1, wherein the bio-based propylene glycol further comprises propylene glycol, butanediol, pentanediol, and hexanediol.

4. The process according to claim 1, wherein the bio-based propylene glycol comprises:
    0-95 wt. % of ethylene glycol, and/or;
    0-50 wt. % of 2,3-butanediol.

5. The process according to claim 2, wherein the biomass comprises edible first generation biomass.

6. The process according to claim 5, wherein the edible first generation biomass comprises corn.

7. The process according to claim 5, wherein the edible first generation biomass comprises sugarcane.

8. The process according to claim 5, wherein the edible first generation biomass comprises non-food second generation biomass of agricultural and/or forestry wastes.

9. The process according to claim 8, wherein the edible non-food second generation biomass of agricultural and/or forestry wastes comprises straw.

10. The process according to claim 8, wherein the edible non-food second generation biomass of agricultural and/or forestry wastes comprises timber.

11. The process according to claim 8, wherein the edible non-food second generation biomass of agricultural and/or forestry wastes comprises bagasse.

12. The process according to claim 3, wherein the bio-based propylene glycol comprises:
    about 5 to about 99 wt. % of propylene glycol;
    about 0 to about 50 wt. % butanediol, excluding the end point of 0;
    about 0 to about 10 wt. % pentanediol, excluding the end point of 0;
    about 0 to about 10 wt. % hexanediol, excluding end point of 0; and
    about 0 to about 10 wt. %, propylene carbonate.

13. The process according to claim 3, wherein the bio-based propylene glycol comprises:
    about 10 to about 95 wt. % of propylene glycol;
    about 0 to about 30 wt. % butanediol, excluding the end point of 0;
    about 0 to about 1 wt. % pentanediol, excluding the end point of 0;
    about 0 to about 1 wt. % hexanediol, excluding end point of 0; and
    about 0 to about 1 wt. %, propylene carbonate.

14. The process of claim 1, wherein step (vi) produces propylene glycol with 99.50% or more purity.

* * * * *